Figure 6:
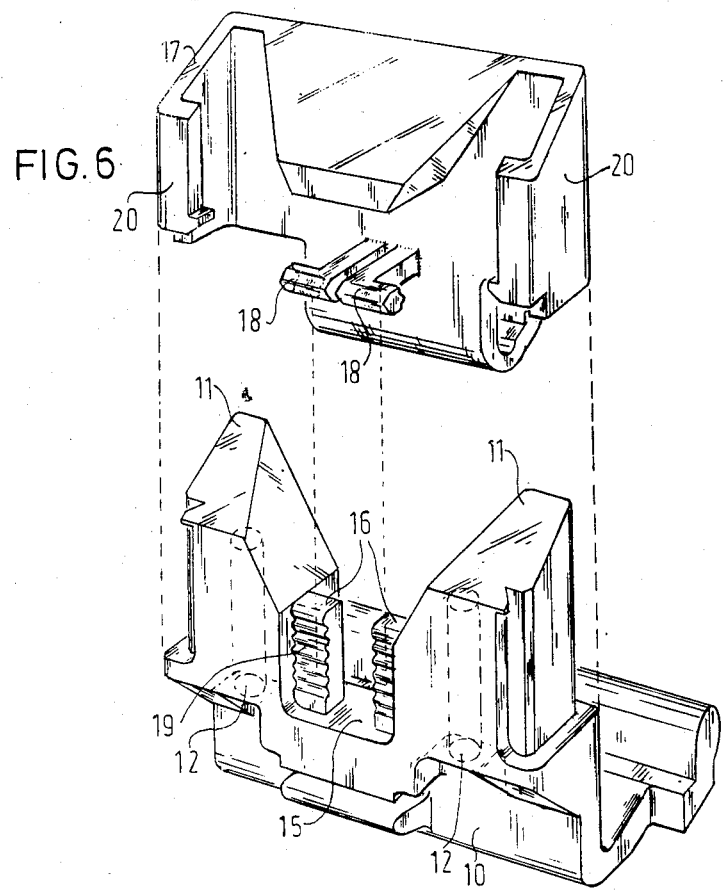

United States Patent [19]

Van Aken

[11] Patent Number: 4,707,847
[45] Date of Patent: Nov. 17, 1987

[54] DEVICE FOR TAKING A PICTURE OF A JAW PART

[75] Inventor: Jan Van Aken, Utrecht, Netherlands

[73] Assignee: 501 Hecopharma B.V., Cuyk, Netherlands

[21] Appl. No.: 709,692

[22] Filed: Feb. 12, 1985

[30] Foreign Application Priority Data

Jun. 15, 1983 [NL] Netherlands .......................... 8302144

[51] Int. Cl.$^4$ ............................................. G03B 42/04
[52] U.S. Cl. .................................... 378/170; 378/168; 378/169
[58] Field of Search ........................ 378/168, 169, 170; 206/455

[56] References Cited

U.S. PATENT DOCUMENTS

| | | |
|---|---|---|
| 1,012,561 | 12/1911 | Ketcham .............................. 378/168 |
| 1,564,269 | 12/1925 | Peyser .................................. 378/169 |
| 1,585,264 | 5/1926 | Rosenthal ............................ 378/168 |
| 2,034,049 | 3/1936 | Levy .................................... 378/170 |
| 2,090,933 | 8/1937 | Bolin . | |
| 2,753,461 | 7/1956 | Goldberg . | |
| 3,745,344 | 7/1973 | Updegrave . | |
| 4,507,798 | 4/1985 | Welander ............................ 378/168 |
| 4,554,676 | 11/1985 | Maldonado et al. ................ 378/170 |

FOREIGN PATENT DOCUMENTS 0078425 5/1983 European Pat. Off. .

Primary Examiner—Craig E. Church
Assistant Examiner—John C. Freeman
Attorney, Agent, or Firm—John P. Snyder

[57] ABSTRACT

A device for recording images of a patient's jaw includes a holder carrying a radiation window disposed externally of the patient's mouth and mounting a carrier disposed within a patient's mouth. A biting element is connected to the carrier and projects toward the window and the carrier provides a surface facing the window and against which a radiation sensitive plate is located. Location and positioning of the plate against the surface is effected by a cap which fits over the carrier. The cap has rounded corners and is formed of flexible material to protect the patient's mouth from injury. The carrier is formed of a first part which attaches to the holder and a second part which is adjustable thereon parallel to the window and the biting element is adjustable laterally on the first part to allow further adjustment of the plate within the patient's mouth. The biting element is provided with a recess for curable material so that the patient's teeth may make a permanent impression to allow the same biting element to be used in a subsequent image making process while assuring the original location of the patient's teeth with respect thereto.

18 Claims, 7 Drawing Figures

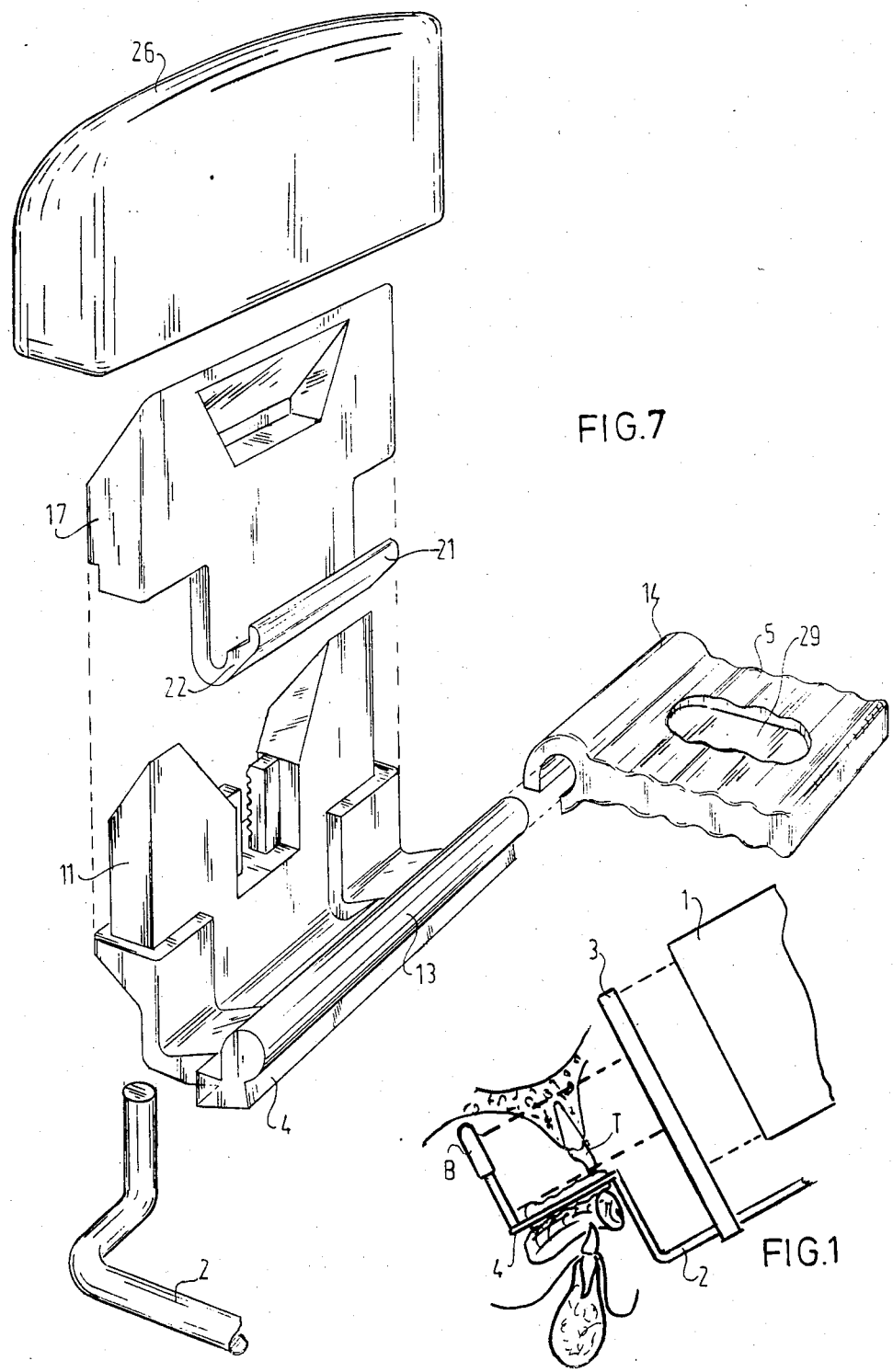

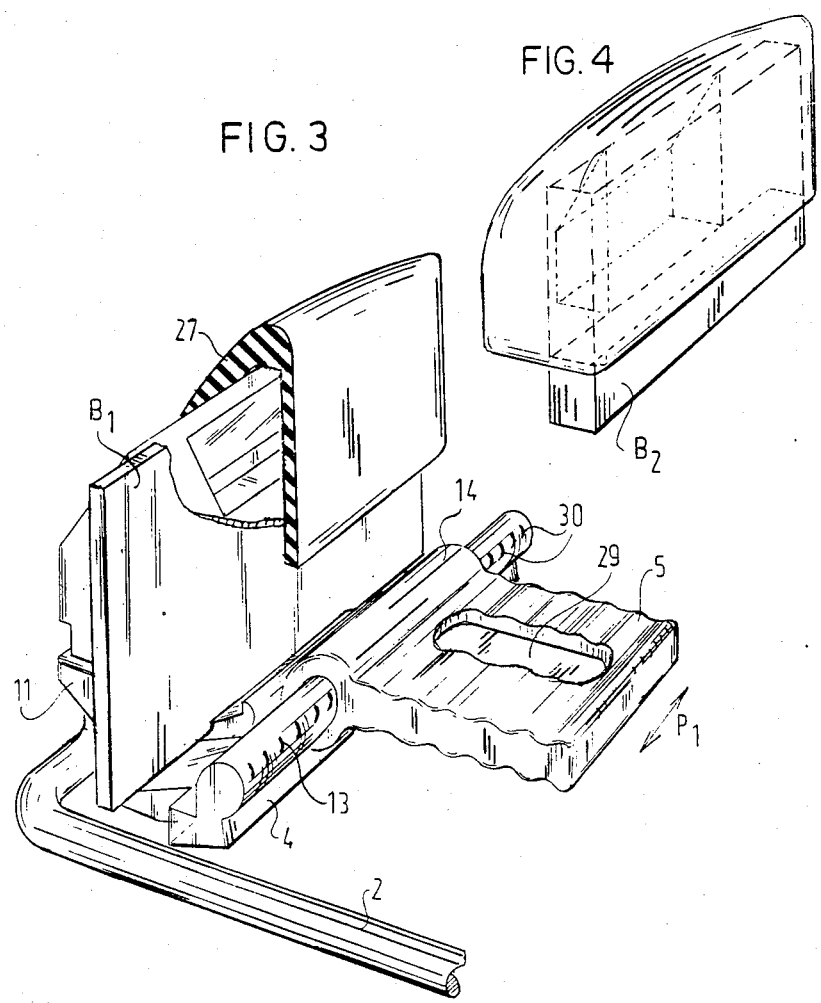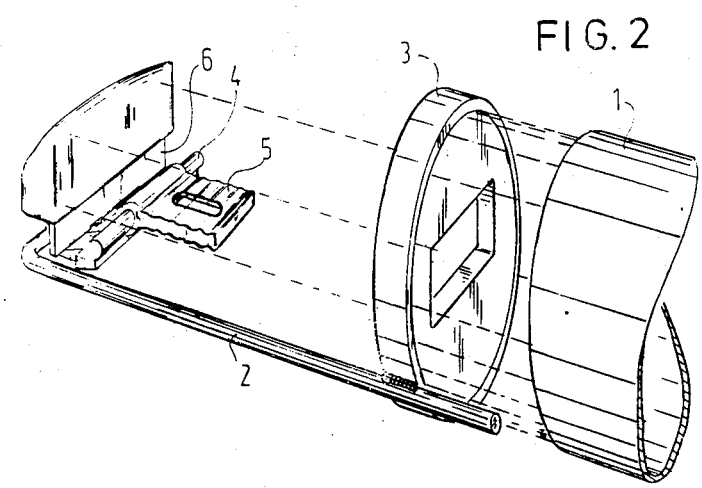

DEVICE FOR TAKING A PICTURE OF A JAW PART

The invention relates to a device for taking a picture of a jaw part with elements such as tooth or molar tooth, said device mainly comprising a holder to be orientated with respect to a source of radiation having a windowed screen to be positioned in front of said source, a carrier arranged at a distance therefrom for retaining a picture plate at a predetermined angle of, for example, 90° to the beam of rays and a biting element extending in the direction of the beam of rays.

Such a device serves to position the picture plate with respect to the beam of rays, which may be an X-ray beam commonly used in dentistry for taking X-ray pictures.

The invention has for its object to improve the device set forth above in a sense that the picture plate can be positioned more accurately than before with respect to the beam of rays determined by the window in the screen, whilst nevertheless the device remains friendly to the user, that is to say, this positioning does not give rise to any appreciable problem to the user and to any appreciable nuisance for the patient.

The invention provides a device which is distinguished in that a releasable cap-shaped positioning member is arranged on the carrier and the picture plate placed thereon for positioning the picture plate with respect to the window.

The cap-shaped positioning member embodying the invention thus has a double function i.e. determination by its shape of the position of the picture plate with respect to the screen and, in addition protection of the patient against nuisance. The conventional picture plates have relatively sharp and/or hard edges, which are now covered by the cap so that these edges will not injure the delicate mucous membrane in the oral cavity. The carrier is preferably provided with a supporting rim of a stepped shape so that picture plates of different thickness can be effectively held in place.

It is furthermore preferred to construct the supporting rim with a back part of the carrier so as to be displaceable in height with respect to the holder so that the picture plate can be displaced transversely of the beam of rays.

According to a further aspect of the invention the biting element is slidable parallel to the supporting rim with respect to the carrier. This has the advantage that the biting element can be positioned at the side of the jaw part to be displayed, which is particularly effective when wisdom teeth have not yet emerged or when elements are lacking.

It is furthermore preferred to provide recesses in the element for receiving a curable mass. By keeping the biting element with the impression it is ensured by this step that, when taking a new picture after some time, the holder can be accurately positioned with respect to the oral cavity so that a correct comparison of pictures taken prior to and after the treatment can be made.

The above mentioned and further features of the invention will become apparent from the following description of the figures of an embodiment.

Figure 5:
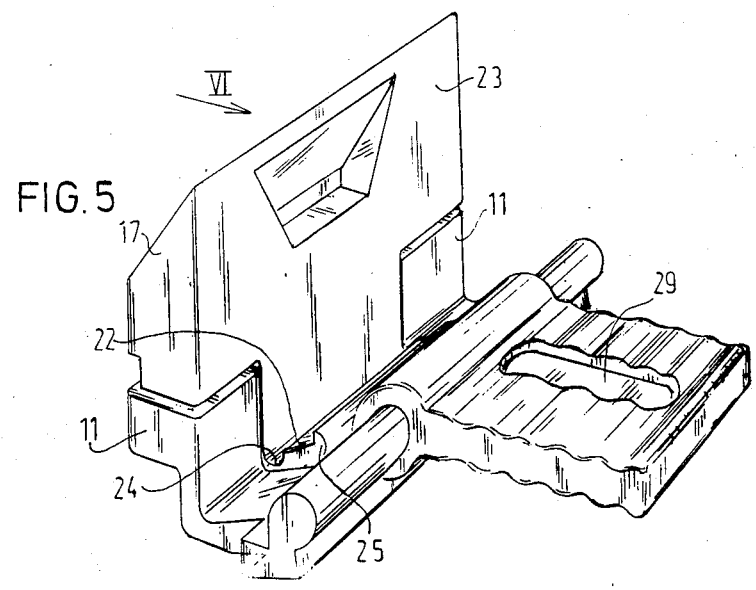

The drawing shows in:

FIG. 1 a schematic disposition of a device embodying the invention with respect to the oral cavity, FIG. 2 a perspective view of the device of FIG. 1, FIG. 3 a perspective view of the carrier with the picture plate placed thereon on an enlarged scale, FIG. 4 a perspective view of the top part of the carrier of FIG. 3 with a different type of picture plate, FIG. 5 a perspective view like that of FIG. 3 of the carrier without the cap, FIG. 6 a perspective view of the rear side of the carrier of FIG. 5 in the direction of the arrow P1, FIG. 7 a perspective view like that of FIG. 3 of the carrier, the various parts being shown separately.

The device shown in the figures mainly comprises a source of radiation 1, which may be of different nature. It may be an X-ray apparatus.

The source of radiation is directed with the aid of a holder 2 carrying a screen 3 having a window for directing and forming a beam of rays from the source 1. At a distance from the screen 3 the holder 2 is provided with a carrier 4 provided with a biting element 5.

FIGS. 1 and 2 it is clearly apparent that the patient's teeth are placed on the biting element 5 in a manner such that the carrier 4 is located in the oral cavity on the rear side of the jaw elements T with respect to the source of radiation 1. The carrier 4 supports a picture plate 6, which is sensitive to the radiation emitted by the source 1 so that a screening image of the jaw with the elements set therein can be made. This technique is known per se and lies beyond the scope of this invention.

Referring to FIGS. 3 to 7 an embodiment of the carrier according to the invention will be described more fully.

The carrier 4 comprises a first spray-cast part 10 provided with two upright posts 11 having a bore 12 for receiving the end of the holder 2. The connection between the part 10 and the holder 2 can be established by clamping effect. On the front side the posts 11 have a ridge 13 along which a sleeve 14 of the biting element 5 can be slid to and fro in the direction of the arrow P1. The ridge 13 has no stops so that the sleeve 14 or the biting element 5 can be entirely slid from the ridge 13 and again be slid onto it.

Between the posts 11 is formed a space 15 into which project two ridges 16 connected with each post. These ridges serve for guiding a back part 17 of the carrier 4 which is displaceable in a direction of height. On the rear side the back part (see FIG. 6) is provided for this purpose with a hook-like bracket 18 perpendicular thereto, the bent-over end of which grips behind each ridge 16. The ridge 16 is furthermore provided with ribs 19 or the like, between which will snap the bent-over end part 18 so that the backpart 17 can be positioned in height with respect to the lower part 10. The back part has furthermore two end flanges 20 gripping around the posts 11 so that a sliding movement in a direction of height is allowed.

On the front side the back part 17 is provided with a foot rim 21, which has a stepped top face 22. It is thus possible to accomodate a picture plate B1 formed by a film suitable for X-rays and being relatively thin in the groove 24 nearest the front face 23. Besides it is possible to accomodate a picture plate B2 of FIG. 4 formed by a thicker, xerographic plate suitable for X-rays in the broader part of the foot between the end rim 25 and the front side 23 of the back part 17.

Finally the back part 17 is associated with a cap-shaped part 26 having a cavity 27 such that it fully covers the back part 17 and the picture plate B1 or B2 respectively.

By this cavity it is ensured that the picture plate B1 is accurately positioned with respect to the back plate 17 in a lateral and upward sense so that also the picture plate is accurately positioned with respect to the screen 3 and the window therein for obtaining the correct picture. The cavity 27 is, of course, adapted to the dimensions of the desired picture plate.

The cap 26 is fully rounded off on the outer side end and it is preferably made from a relatively soft, elastic X-ray pervious material so that not only a satisfactory clamping effect on the picture plate B and the back part 17 can be obtained, but also the relatively weak mucous membrane in the oral cavity will not be injured.

The biting element 5 may have a recess 29 for receiving a curable mass to be arranged in advance. The tooth or molar tooth will leave an impression in this curable mass so that re-arrangement of the biting element 5 in the mouth is facilitated when afterwards again a picture has to be taken to judge variations in the patient.

For accurately positioning the biting element with respect to the carrier 4 the back 13 may have marking lines 30, which can be noted on the picture and the biting element 5.

The invention is not limited to the embodiment described above, since within the scope of the invention various modifications are possible.

For example, the connection of the carrier 4 with respect to the holder 2 can be varied in dependence on the plate in the oral cavity for the picture carrier. As a matter or course, guiding and locking of the back part 17 displaceable in height may be designed in any desired manner.

What is claimed is:

1. A device for positioning a radiation-sensitive plate within a patient's mouth in predetermined relation to a window through which radiation is directed and which is disposed externally of the patient's mouth, which comprises the combination of a horizontally elongate holder and a window carried by said holder adjacent one end thereof, a carrier connected to said holder adjacent the opposite end thereof and having a portion generally parallel to the window presenting a support surface disposed in spaced, generally opposed relation to said window so that the carrier is positioned in the patient's mouth by the opposite end of the holder while the window is positioned outside the patient's mouth by the one end of the holder, a biting element connected with said carrier and projecting therefrom toward said window and having a generally flat portion so as to be engaged between the patient's teeth, and cap means having a recess shaped generally in conformity with said portion of the carier and fitting over said portion of the carrier for releasably locating and positioning a radiation sensitive plate against said surface in aligned relation to said window.

2. A device as defined in claim 1 wherein said means is in the form of a cap having rounded off corners.

3. A device as defined in claim 1 wherein said means is formed of flexible material.

4. A device as defined in claim 2 wherein said cap is formed of flexible material.

5. A device as defined in claim 1 wherein said portion of the carrier which is generally parallel to the window includes a first part connected with said holder and a second part defining said support surface and adjustably connected with the first part to vary the position of said support surface with respect to said window.

6. A device as defined in claim 1 wherein said carrier includes a first part connected with said holder and a second part adjustably connected with the first part to vary the position of said surface with respect to said window.

7. A device as defined in claim 6 wherein said second part is providing with a step adjacent one boundary of said surface for receiving and locating an edge of the radiation sensitive plate therein.

8. A device for positioning a radiation-sensitive plate within a patient's mouth in predetermined relation to a radiation window disposed externally of the patient's mouth, which comprises the combination of a holder and a radiation window carried by said holder, a carrier connected to said holder and having a support surface disposed in spaced, generally opposed relation to said window so as to be positioned in the patient's mouth, a biting element connected with said carrier and projecting therefrom toward said window and having a generally flat portion so as to be gripped between the patient's teeth, and means fitting over said carrier for releasably locating and positioning a radiation sensitive plate against said surface in aligned relation to said window, said carrier being provided with a step adjacent one boundary of said surface for receiving and locating an edge of the radiation sensitive plate therein, said biting element being slidable relative to said carrier substantially parallel to said window.

9. A device as defined in claim 8 wherein said biting element is provided with a recess for receiving a mass of curable material to take an impression of the patient's teeth so as to locate the biting element subsequent to first use thereof in the same relation to such teeth.

10. A device for positioning a radiation-sensitive plate within a patient's mouth in predetermined relation to a radiation window disposed externally of the patient's mouth, which comprises the combination of a holder and a radiation window carried by said holder, a carrier connected to said holder and having a support surface disposed in spaced, generally opposed relation to said window so as to be positioned in the patient's mouth, a biting element connected with said carrier and projecting therefrom toward said window and having a generally flat portion so as to be gripped between the patient's teeth, and means fitting over said carrier for releasably locating and positioning a radiation sensitive plate against said surface in aligned relation to said window, said carrier includes a first part connected with said holder and a second part adjustably connected with the first part to vary the position of said surface with respect to said window, said biting element being slidable relative to said carrier substantially parallel to said window.

11. A device as defined in claim 10 wherein said biting element is provided with a recess for receiving a mass of curable material to take an impression of the patient's teeth so as to locate the biting element subsequent to first use thereof in the same relation to such teeth.

12. A device for positioning a radiation-sensitive plate within a patient's mouth in predetermined relation to a window disposed externally of the patient's mouth and through which radiation is directed, which comprises the combination of a horizontally extending holder and a window through which radiation is to be admitted disposed in fixed relation on said holder adjacent one end of the holder, a first carrier part connected to said holder adjacent the opposite end of the holder in spaced relation to said window so as to be positioned in the patient's mouth, a biting element connected with said first part and projecting therefrom toward said window and having a generally flat portion so as to be engaged between the patient's teeth, a second part carried by said first part for movement relative to the first part and generally parallel to said window and presenting a radiation-sensitive plate supporting surface generally parallel to said window, said first part being slidable relative to said biting element in a direction generally parallel to said window, said second part having a step along a boundary of said surface, and cap means having a recess shaped generally in conformity with the shape of said second part and fitting over a portion of said second part remote from said step for releasably locating a radiation sensitive plate against said support surface and within said step in aligned relation to said window.

13. A device as defined in claim 12 wherein said means is in the form of a radiation permeable cap fitted over said second part.

14. A device as defined in claim 13 wherein said cap is formed of flexible material.

15. A device for positioning a radiation-sensitive plate within a patient's mouth, which comprises the combination of a biting element so as to be engaged between a patient's teeth, a window connected with the biting element in spaced relation thereto, a carrier connected with the biting element in spaced relation thereto and to the window so that the biting element is between the carrier and the window, said window defining an opening through which radiation is to be directed so as to impinge upon a radiation-sensitive plate held against said carrier, said carrier having a portion defining a support surface disposed in spaced, generally opposed relation to the opening defined by said window, said surface being flat and generally rectangular and said carrier including a stepped portion adjacent an edge of said support surface for positively locating a radiation-sensitive plate with respect to the support surface, and a resilient cap having a recess conforming generally to the shape of said portion so as to be detachable fitted over said portion of the carrier to cooperate with said stepped portion in holding a radiation-sensitive plate in face-to-face contact against said support surface and in aligned relation to said window.

16. A device as defined in claim 15 including a horizontally elongate holder, said window being mounted directly on said holder and said carrier also being mounted directly on said holder, and said biting element being mounted directly on said carrier so that the carier is held in position by the patient's teeth engaging the biting element and the window is connected to the carrier through the holder.

17. A device as defined in claim 15 wherein said carrier is of multi-part form including a first part directly connected to the biting element and a second part defining said portion, said second part being connected to the first part for adjusted movement relative thereto generally parallel to said window.

18. A device as defined in claim 17 including a horizontally elongate holder, said window being mounted directly on said holder and said carrier also being mounted directly on said holder, and said biting element being mounted directly on said carrier so that the carier is held in position by the patient's teeth engaging the biting element and the window is connected to the carrier through the holder.

* * * * *